United States Patent
Doron

(10) Patent No.: US 11,213,249 B2
(45) Date of Patent: Jan. 4, 2022

(54) AUTOMATED SYSTEM FOR CONTROLLING THE BLOOD GLUCOSE LEVEL OF A PATIENT

(71) Applicant: Commissariat à l'Énergie Atomique et aux Énergies Alternatives, Paris (FR)

(72) Inventor: Eléonore Doron, La Tronche (FR)

(73) Assignee: Commissariat à l'Énergie Atomique et aux Énergies Alternatives, Paris (FR)

( * ) Notice: Subject to any disclaimer, the term of this patent is extended or adjusted under 35 U.S.C. 154(b) by 220 days.

(21) Appl. No.: 16/334,812

(22) PCT Filed: Sep. 19, 2017

(86) PCT No.: PCT/FR2017/052512
§ 371 (c)(1),
(2) Date: Mar. 20, 2019

(87) PCT Pub. No.: WO2018/055284
PCT Pub. Date: Mar. 29, 2018

(65) Prior Publication Data
US 2020/0015738 A1     Jan. 16, 2020

(30) Foreign Application Priority Data
Sep. 21, 2016    (FR) ..................... 1658882

(51) Int. Cl.
*A61B 5/00*      (2006.01)
*A61B 5/145*     (2006.01)
(Continued)

(52) U.S. Cl.
CPC ........ *A61B 5/4839* (2013.01); *A61B 5/14532* (2013.01); *A61M 5/1723* (2013.01);
(Continued)

(58) Field of Classification Search
CPC .............. A61B 5/4839; A61B 5/14532; A61B 2560/0228; A61B 2560/0223;
(Continued)

(56) References Cited

U.S. PATENT DOCUMENTS

| | | | |
|---|---|---|---|
| 2005/0203360 A1* | 9/2005 | Brauker | ............... A61B 5/7264 600/345 |
| 2008/0183060 A1 | 7/2008 | Steil et al. | |

(Continued)

FOREIGN PATENT DOCUMENTS

| | | | |
|---|---|---|---|
| GB | 2 436 873 A1 | 10/2007 | |
| GB | 2436873 A * | 10/2007 | .......... A61M 5/1723 |
| JP | 2000-503556 A | 3/2000 | |
| JP | 2015-165970 A | 9/2015 | |
| WO | WO 2007/116226 A2 | 10/2007 | |

OTHER PUBLICATIONS

Hovorka et al., Nonlinear model predictive control of glucose concentration in subjects with type 1 diabetes: Controlling glucose. Physiological Measurement. 2004:25('4'):905-20. (Year: 2004).*

(Continued)

*Primary Examiner* — Bhisma Mehta
*Assistant Examiner* — Neeraja Gollamudi
(74) *Attorney, Agent, or Firm* — Wolf, Greenfield & Sacks, P.C.

(57) ABSTRACT

A blood sugar regulation system including: a blood sugar sensor; an insulin injection device; and a processing and control unit predicting the future evolution of the blood sugar based on a physiological model and accordingly controlling the insulin injection device, wherein the processing and control unit is capable of: a) implementing a calibration of the model by taking into account a history of the measured blood sugar; b) at the end of the calibration step, determining whether the model is satisfactory or not based on at least one numerical indicator representative of the error between the blood sugar estimated based on the (Continued)

model and the real blood sugar measured by the sensor; and c) if the quality of the model is not satisfactory, controlling the insulin injection device without taking into account the predictions made from the model.

9 Claims, 3 Drawing Sheets

(51) Int. Cl.
*A61M 5/172* (2006.01)
*A61M 5/142* (2006.01)

(52) U.S. Cl.
CPC .. *A61B 2560/0228* (2013.01); *A61M 5/14244* (2013.01); *A61M 2005/14208* (2013.01); *A61M 2005/1726* (2013.01); *A61M 2205/50* (2013.01); *A61M 2230/201* (2013.01)

(58) Field of Classification Search
CPC .. A61B 5/14503; A61B 5/746; A61M 5/1723; A61M 5/14224; A61M 5/142; A61M 2005/14208; A61M 2205/50; A61M 2205/502; A61M 2205/52; A61M 2230/201; A61M 2205/18; G16H 20/17; G16H 50/20; G16H 10/40

See application file for complete search history.

(56) References Cited

U.S. PATENT DOCUMENTS

| 2012/0123234 | A1* | 5/2012 | Atlas | A61M 5/1723 600/365 |
| 2014/0066884 | A1* | 3/2014 | Keenan | A61M 5/172 604/504 |
| 2014/0073892 | A1* | 3/2014 | Randloev | A61B 5/7275 600/365 |

OTHER PUBLICATIONS

International Search Report and Written Opinion for International Application No. PCT/FR2017/052512, dated Jan. 26, 2018.
Hovorka et al., Nonlinear model predictive control of glucose concentration in subjects with type 1 disbetes; Controlling glucose. Physiological Measurement. 2004;25(4):905-20.
Rawlings et al., Model predictive control: Theory and Design. http://jbrwww.che.wisc.edu/home/jbraw/mpc/electronic-book.pdf. Dated Aug. 19, 2012, last accessed May 24, 2017. 724 pages.
International Preliminary Report on Patentability for International Application No. PCT/FR2017/052512, dated Mar. 26, 2019.
Hovorka et al., Nonlinear model predictive control of glucose concentration in subjects with type 1 diabetes. Physiological measurement. Jul. 22, 2004;25(4):905-20.

* cited by examiner

AUTOMATED SYSTEM FOR CONTROLLING THE BLOOD GLUCOSE LEVEL OF A PATIENT

This application is a national stage filing under 35 U.S.C. § 371 of International Patent Application Serial No. PCT/FR2017/052512, filed Sep. 19, 2017, which claims priority to French patent application FR16/58882, filed on Sep. 21, 2016. The entire contents of these applications are incorporated herein by reference in their entirety.

BACKGROUND

The present application relates to the field of automated blood sugar regulation systems, also called artificial pancreases.

DISCUSSION OF THE RELATED ART

An artificial pancreas is a system enabling to automatically regulate the insulin intake of a diabetic patient based on his/her blood sugar history, on his/her meal history, and on his/her insulin injection history.

MPC-type regulation systems or model predictive control systems, where the regulation of the delivered insulin dose takes into account a prediction of the future evolution of the patient's blood sugar, obtained from a physiological model describing the assimilation of insulin by the patient's body and its impact on the patient's blood sugar, are here more particularly considered.

It would be desirable to be able to improve the performance of model predictive control artificial pancreases and, more particularly, to be able to improve the quality of the prediction of the patient's future blood sugar, to be able to control with a better relevance insulin intakes and to limit risks of placing the patient in a hyperglycemia or hypoglycemia situation.

It would further be desirable to be able to limit risks for the patient due to a possible failure of the physiological model used to predict the patient's future blood sugar.

SUMMARY

Thus, an embodiment provides an automated system of regulation of a patient's blood sugar, comprising:
  a blood sugar sensor;
  an insulin injection device; and
  a processing and control unit capable of predicting the future evolution of the patient's blood sugar from a physiological model and of controlling the insulin injection device by taking the prediction into account,
  wherein:
  the physiological model comprises a differential equation system describing the time variation of a plurality of state variables; and
  the processing and control unit is capable of implementing a step of automatic calibration of the physiological model comprising a step of estimation of initial values of the state variables by minimization of a quantity representative of the error, during a past observation period, between the blood sugar estimated based on the physiological model and the blood sugar measured by the sensor.

According to an embodiment, the quantity is representative of the area between a first curve $\hat{g}$ representative of the time variation of the blood sugar estimated based on the model over the observation period, and a second curve g representative of the time variation of the blood sugar measured by the sensor over the observation period.

According to an embodiment, the quantity is defined as follows:

$$m = \frac{1}{\Delta T} \sum_{t=t_0}^{t_0+\Delta T} |g(t) - \hat{g}(t)|^2$$

where t is a discretized time variable, is $t_0$ the time of beginning of the observation phase, and $t_0+\Delta T$ is the end time of the observation phase.

According to an embodiment, the calibration method further comprises a step of estimation of parameters of the differential equation system by minimization of said quantity.

According to an embodiment, the calibration method comprises a plurality of successive iterations of the following steps a) and b):
  a) estimating the parameters of the differential equation system by minimization of said quantity by setting the initial values of the state variables; and
  b) estimating the initial values of the state variables by minimization of said quantity by setting the parameters of the differential equation system.

According to an embodiment, at the first iteration of step a), the initial values of the state variables are analytically determined by making the assumption that all the derivatives of the differential equation system are zero.

According to an embodiment, the simulate the evolution of the patient's blood sugar based on the physiological model, the processing and control unit takes into account the history of the insulin injected to the patient by the injection device and the history of the glucose ingested by the patient.

According to an embodiment, the physiological model is Hovorka's model.

Another embodiment provides a method of automated regulation of a patient's blood sugar, comprising:
  a step of calculating, by means of a processing and control unit, a prediction of the future evolution of the patient's blood sugar based on a physiological model comprising a differential equation system describing the time variation of a plurality of state variables;
  a step of controlling an insulin injection device taking this prediction into account; and
  a step of automatic calibration of the physiological model comprising a step of estimation of initial values of the state variables by minimization of a quantity representative of the error, during a past observation period, between the blood sugar estimated based on the physiological model and the blood sugar measured on the patient by a blood sugar sensor.

According to an embodiment, the method further comprises a step of estimation of parameters of the differential equation system by minimization of said quantity.

According to an embodiment, the calibration step comprises a plurality of successive iterations of the following steps a) and b):
  a) estimating the parameters of the differential equation system by minimizing said quantity by setting the initial values of the state variables; and
  b) estimating the initial values of the state variables by minimizing said quantity by setting the parameters of the differential equation system.

Another embodiment provides an automated system of regulation of a patient's blood sugar, comprising:

a blood sugar sensor;

an insulin injection device; and a processing and control unit capable of predicting the future evolution of the patient's blood sugar based on a physiological model and of controlling the insulin injection device by taking the prediction into account, wherein the processing and control unit is capable of:

a) implementing a step of automatic calibration of the physiological model by taking into account a history of the blood sugar measured by the sensor during a past observation period;

b) at the end of the calibration step, determining whether the model is satisfactory or not based on at least one numerical indicator representative of the error between the blood sugar estimated based on the model and the real blood sugar measured by the sensor; and c) if the quality of the model is not satisfactory, controlling the insulin injection device without taking into account the prediction made from the model.

According to an embodiment, the numerical indicator comprises an indicator m representative of the area between a first curve $\hat{g}$ representative of the time variation of the blood sugar estimated based on the model over the observation period, and a second curve g representative of the time variation of the blood sugar measured by the sensor over the observation period.

According to an embodiment, indicator m is defined as follows:

$$m = \frac{1}{\Delta T} \sum_{t=t_0}^{t_0+\Delta T} |g(t) - \hat{g}(t)|^2$$

where t is a discretized time variable, is $t_0$ the time of beginning of the observation phase, and $t_0+\Delta T$ is the end time of the observation phase.

According to an embodiment, the numerical indicator comprises an indicator $m_1$ representative of the difference between the blood sugar estimated based on the model and the blood sugar measured by the sensor at a given time.

According to an embodiment, the numerical indicator comprises an indicator $m_2$ representative of the difference between the derivative of the blood sugar estimated based on the model and the derivative of the blood sugar measured by the sensor at a given time.

According to an embodiment, at step c), the control of the insulin injection device is a model predictive control based on a simplified physiological model.

According to an embodiment, at step c), the insulin injection device is controlled to deliver preprogrammed insulin doses corresponding to a reference basal rate prescribed to the patient.

According to an embodiment, the physiological model comprises a differential equation system describing the time variation of a plurality of state variables, and step a) of automatic calibration of the model comprises a step of estimation of parameters of the differential equation system by minimization of a quantity representative of the error, during a past observation period, between the blood sugar estimated based on the physiological model and the blood sugar measured by the sensor.

According to an embodiment, step a) of automatic calibration of the model further comprises a step of determination of initial values of the state variables.

Another embodiment provides a method of automated regulation of a patient's blood sugar, comprising:

a step of calculating, by means of a processing and control unit, a prediction of the future evolution of the patient's blood sugar based on a physiological model; and a step of control of an insulin injection device taking this prediction into account, the method further comprising:

a) a step of automatic calibration of the physiological model taking into account a history of the blood sugar measured by a blood sugar sensor during a past observation period;

b) at the end of the calibration step, a step of determination of the quality of the physiological model based on at least one numerical indicator representative of the error between the blood sugar estimated based on the model and the real blood sugar measured by the sensor; and c) if the quality of the model is considered unsatisfactory, a step of control of the insulin injection device without taking into account the prediction made from the model.

BRIEF DESCRIPTION OF THE DRAWINGS

The foregoing and other features and advantages will be discussed in detail in the following non-limiting description of specific embodiments in connection with the accompanying drawings, among which.

DETAILED DESCRIPTION

Figure 1:
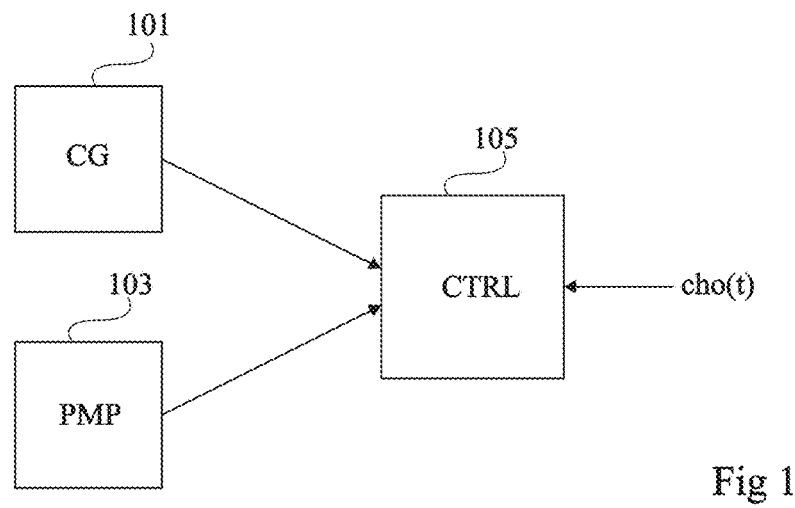
FIG. 1 schematically shows, in the form of blocks, an embodiment of an automated system of regulation of a patient's blood sugar.

The same elements have been designated with the same reference numerals in the different drawings. For clarity, only those elements which are useful to the understanding of the described embodiments have been shown and are detailed. In particular, the blood sugar measurement device and the insulin injection device of the described regulation system have not been detailed, the described embodiments being compatible with all or most known blood sugar measurement and insulin injection devices. Further, the hardware implementation of the processing and control unit of the described regulation system has not been detailed, the forming of such a processing and control unit being within the abilities of those skilled in the art based on the described functional indications.

FIG. 1 schematically shows in the form of blocks an embodiment of an automated system of regulation of a patient's blood sugar.

The system of FIG. 1 comprises a sensor 101 (CG) capable of measuring the patient's blood sugar. In normal operation, sensor 101 may be permanently positioned on or inside of the patient's body, for example, at the level of the abdomen. Sensor 101 is for example a CGM-type ("Continuous Glucose Monitoring") sensor, that is, a sensor capable of continuously measuring (for example, at least once per minute) the patient's blood sugar. Sensor 101 is for example a subcutaneous blood sugar sensor.

The system of FIG. 1 further comprises an insulin injection device 103 (PMP), for example, a subcutaneous injection device. Device 103 is for example, an automatic injection device of insulin pump type, comprising an insulin reservoir connected to an injection needle implanted under the patient's skin, and the pump may be electrically controlled to automatically inject determined insulin doses at determined times. In normal operation, injection device 103 may be permanently positioned inside of or on the patient's body, for example, at the level of the abdomen.

The system of FIG. 1 further comprises a processing and control unit 105 (CTRL) connected on the one hand to blood sugar sensor 101, for example, by a wire link or by a radio (wireless) link, and on the other hand to injection device 103, for example, by wire or radio link. In operation, processing and control unit 105 is capable of receiving the data relative to the patient's blood sugar measured by sensor 101, and of electrically controlling device 103 to inject to the patient determined insulin doses at determined times. In this example, processing and control unit 105 is further capable of receiving, via a user interface, not detailed, data cho(t) representative of the time variation of the quantity of glucose ingested by the patient.

Processing and control unit 105 is capable of determining the insulin doses to be injected to the patient by taking into account, in particular, the history of the blood sugar measured by sensor 101, the history of insulin injected by device 103, and the history of glucose ingestion by the patient. To achieve this, processing and control unit 105 comprises a digital calculation circuit (not detailed), for example comprising a microprocessor. Processing and control unit 105 is for example a mobile device carried by the patient all along the day and/or the night, for example, a smartphone-type device configured to implement a regulation method of the type described hereafter.

In the embodiment of FIG. 1, processing and control unit 105 is capable of determining the quantity of insulin to be delivered to the patient by taking into account a prediction of the future evolution of his/her blood sugar over time. More particularly, processing and control unit 105 is capable, based on the injected insulin history and the ingested blood sugar history, and based on a physiological model describing the assimilation of insulin by the patient's body and its impact on blood sugar, of determining a curve representative of the expected evolution of the patient's blood sugar over time, during a period to come, for example, a period from 1 to 10 hours. Taking this curve into account, processing and control unit 105 determines the insulin doses to be injected to the patient during the period to come, so that the patient's real blood sugar (as opposed to the blood sugar estimated based on the physiological model) remains within acceptable limits, and in particular to limit risks of hyperglycemia or of hypoglycemia. In such an operating mode, as will be explained in further detail hereafter, the data relative to the real blood sugar measured by sensor 101 are mainly used for purposes of calibration of the physiological model.

Figure 2:
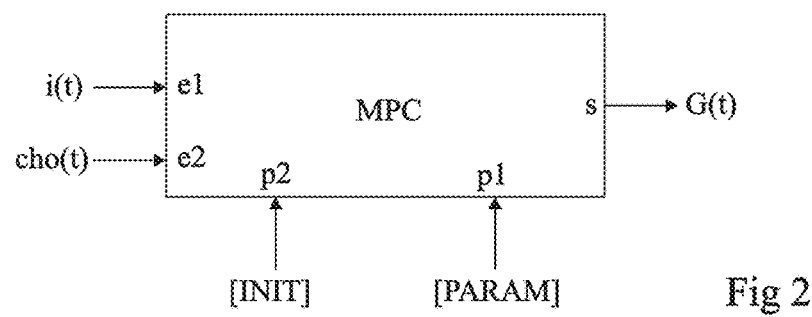
FIG. 2 is a simplified representation of a physiological model used in the system of FIG. 1 to predict the future evolution of the patient's blood sugar.

FIG. 2 is a simplified representation of a MPC physiological model used in the system of FIG. 1 to predict the future evolution of the patient's blood sugar. In FIG. 2, the model is shown in the form of a processing block comprising:

an input e1 having a signal i(t) representative of the evolution, over time t, of the quantity of insulin injected to the patient, applied thereto;

an input e2 having a signal cho(t) representative of the evolution, over time t, of the quantity of glucose ingested by the patient, applied thereto; and an output s delivering a signal G(t) representative of the evolution, over time t, of the patient's blood sugar.

The MPC physiological model is a compartmental model comprising, in addition to input variables i(t) and cho(t) and output variable G(t), a plurality of state variables corresponding to physiological variables of the patient, varying over time. The time variation of the state variables is ruled by a differential equation system comprising a plurality of parameters shown in FIG. 2 by a vector [PARAM] applied to an input p1 of the MPC block. The response of the physiological model is further conditioned by the initial states or initial values assigned to the state variables, represented in FIG. 2 by a vector [INIT] applied to an input p2 of the MPC block.

Figure 3:
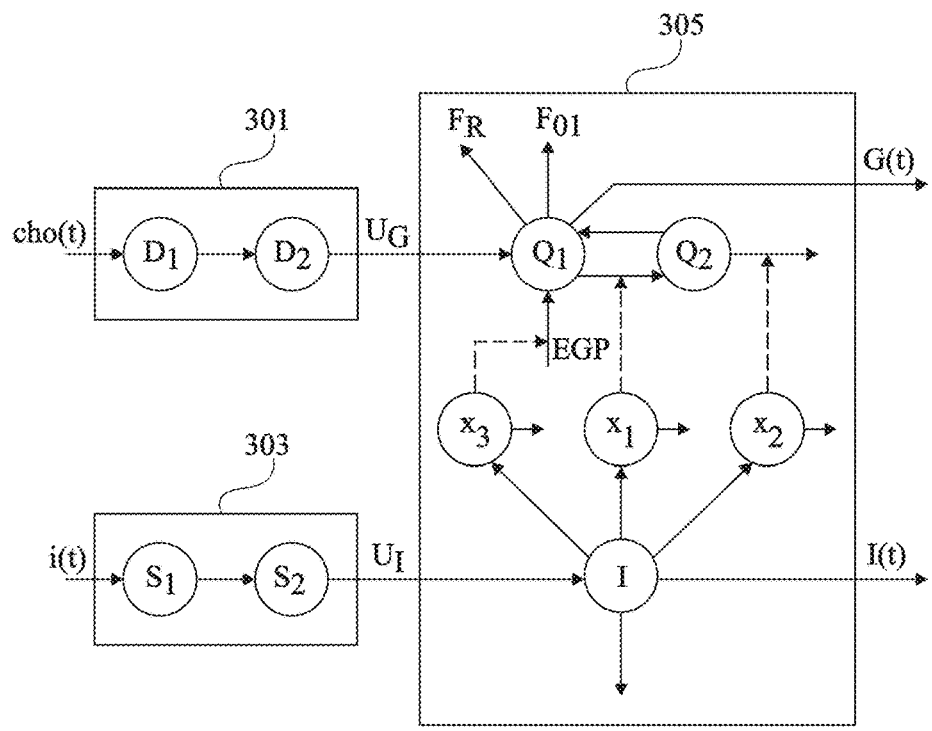
FIG. 3 is a diagram showing in further detail an embodiment of the physiological model of FIG. 2.

FIG. 3 is a diagram showing in further detail a (non-limiting) example of the MPC physiological model used in the system of FIG. 1 to predict the future evolution of the patient's blood sugar. This example of model, known as the Hovorka model, is described in further detail in the article entitled "Nonlinear model predictive control of glucose concentration in subjects with type 1 diabetes" of Roman Hovorka et al. (Physiol Meas. 2004; 25:905-920), and in the article entitled "Partitioning glucose distribution/transport, disposal, and endogenous production during IVGTT", of Roman Hovorka et al. (Am J Physiol Endocrinol Metab 282: E992-E1007, 2002).

The physiological model of FIG. 3 comprises a first bicompartmental sub-model 301 describing the effect of a dietary intake of glucose on the rate of occurrence of glucose in the blood plasma. Sub-model 301 takes as an input the quantity of ingested glucose cho(t), for example, in mmol/min, and outputs a rate $U_G$ of glucose absorption in the blood plasma, for example, in mmol/min. Sub-model 301 comprises two state variables $D_1$ and $D_2$ respectively corresponding to masses of glucose, for example, in mmol, in first and second compartments.

The model of FIG. 3 further comprises a second bicompartmental sub-model 303 describing the absorption, in the blood plasma, of the insulin delivered to the patient. Sub-model 303 takes as an input quantity of insulin i(t) injected to the patient, for example, in mU/min, and outputs a rate $U_I$ of insulin absorption in the blood plasma, for example, in mU/min. Sub-model 303 comprises two state variables $S_1$ and $S_2$ respectively corresponding to insulin masses, for example, in mmol, in first and second compartments.

The model of FIG. 3 further comprises a third sub-model 305 describing the glucose regulation by the patient's body. Sub-model 305 takes as inputs the absorption rates $U_G$ of glucose and $U_I$ of insulin, and output the blood sugar G(t), that is, the glucose concentration in the blood plasma, for example in mmol/l. Sub-model 305 comprises six state variables $Q_1$, $Q_2$, $x_3$, $x_1$, $x_2$, I. Variables Q1 and Q2 respectively correspond to glucose masses, for example, in mmol, in first and second compartments. Variables $x_1$, $x_2$, $x_3$ are unit-less variables representing each of the actions of insulin on the glucose kinetics. Variable I corresponds to the insulinemia, that is, the insulin concentration in the blood plasma, for example, in mU/l.

Hovorka's model is ruled by the following equation system:

$$G(t) = \frac{Q_1(t)}{V_G}$$

$$\frac{dQ_1}{dt} = -\left[\frac{F_{01}^c}{V_G \cdot G(t)} + x_1(t)\right] \cdot Q_1(t) + k_{12}Q_2(t) - F_R + EGP_0 \cdot [1 - x_3(t)] + U_G(t)$$

$$\frac{dQ_2}{dt} = x_1(t) \cdot Q_1(t) - [k_{12} + x_2(t)] \cdot Q_2(t)$$

$$\frac{dx_1}{dt} = -k_{b1} \cdot x_1(t) + k_{a1} \cdot I(t)$$

$$\frac{dx_2}{dt} = -k_{b2} \cdot x_2(t) + k_{a2} \cdot I(t)$$

$$\frac{dx_3}{dt} = -k_{b3} \cdot x_3(t) + k_{a3} \cdot I(t)$$

$$\frac{dS_1}{dt} = i(t) - k_a \cdot S_1(t)$$

$$\frac{dS_2}{dt} = k_a \cdot S_1(t) - k_a \cdot S_2(t)$$

$$\frac{dI}{dt} = \frac{k_a \cdot S_2(t)}{V_I} - k_e \cdot I(t)$$

$$\frac{dD_1}{dt} = cho(t) - \frac{D_1(t)}{t_{max}}$$

$$\frac{dD_2}{dt} = \frac{D_1(t)}{t_{max}} - \frac{D_2(t)}{t_{max}}$$

$$U_G = \frac{D_2(t)}{t_{max}}$$

with: $F_{01}^c = \frac{F_{01} \cdot G(t)}{0.85 \cdot (G(t) + 1.0)}$ $$F_R = \begin{cases} R(G-9) \cdot V_G & \text{if } G > 9 \\ 0 & \text{otherwise} \end{cases}$$

In this equation system, quantities $V_G$, $F_{01}$, $k_{12}$, $F_R$, $EGP_0$, $k_{b1}$, $k_{a1}$, $k_{b2}$, $k_{a2}$, $k_{b3}$, $k_{a3}$, $k_a$, $V_I$, $k_e$, and $t_{max}$ are parameters. $V_G$ corresponds to the glucose distribution volume, for example, in liter, $F_{01}$ corresponds to a transfer rate of the non-insulin dependent glucose, for example, in mmol/min, $k_{12}$ corresponds to a constant of the transfer rate between the two compartments of sub-model 305, for example, in min$^{-1}$, $k_{a1}$, $k_{a2}$, $k_{a3}$ correspond to insulin deactivation rate constants, for example, in min$^{-1}$, $F_R$ corresponds to a glucose urination, for example, in mmol/min, $EGP_0$ corresponds to an endogenous production of glucose, for example, in min$^{-1}$, $k_{b1}$, $k_{b2}$, and $k_{b3}$ correspond to insulin activation rate constants, for example, in min$^{-1}$, $k_a$ corresponds to a subcutaneously injected insulin absorption rate constant, for example, in min$^{-1}$, $V_I$ corresponds to the insulin distribution volume, for example, in liters, $k_e$ corresponds to a rate of elimination of the plasma's insulin, for example, in min$^{-1}$, and $t_{max}$ corresponds to the time elapsed until the absorption peak of the glucose ingested by the patient, for example, in min. These fifteen parameters correspond to vector [PARAM] of the representation of FIG. 2. Vector [INIT] comprises ten values corresponding to the initial values (at a time $t_0$ of beginning of a phase of simulation of the patient's behavior based on the model) assigned to the ten state variables $D_1$, $D_2$, $S_1$, $S_2$, $Q_1$, $Q_2$, $x_1$, $x_2$, $x_1$, and I of the model.

Among the parameters of vector [PARAM], some may be considered as constant for a given patient. These are for example parameters $k_{12}$, $k_{a1}$, $k_{a2}$, $k_{a3}$, $k_a$, $k_e$, $V_I$, $V_G$, and $t_{max}$. Other parameters, called time-dependent parameters hereafter, are however capable of varying over time, for example, parameters $k_{b1}$, $k_{b2}$, $k_{b3}$, $EGP_0$, $F_{01}$, and $F_R$. Due to this variability of certain parameters of the system, it is in practice necessary to regularly recalibrate the model used, for example, every 1 to 20 minutes, to make sure that the predictions of the model remain relevant. Such an update of the model, called model personalization, should be capable of being carried out automatically by the system of FIG. 1, that is, without requiring physically measuring the time-dependent parameters of the system on the patient and then to transmit them to processing and control unit 105.

Figure 4:
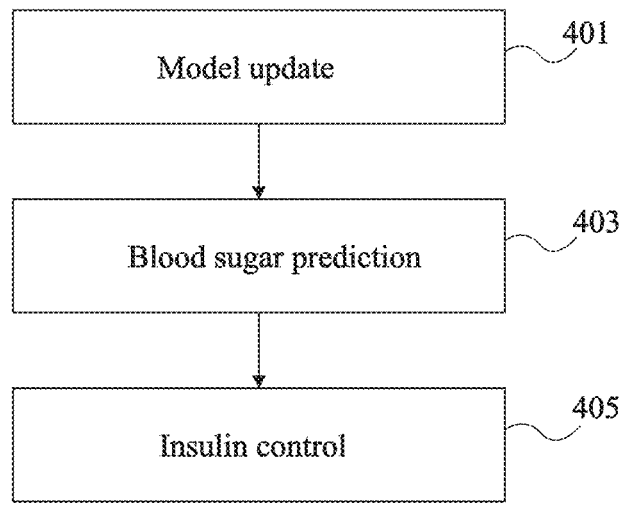
FIG. 4 is a diagram illustrating an example of an automated blood sugar regulation method implemented by the system of FIG. 1.

FIG. 4 is a diagram illustrating an example of an automated blood sugar regulation method implemented by the system of FIG. 1.

This method comprises a step 401 of recalibration or update of the model, which may for example be repeated at regular intervals, for example, every 1 to 20 minutes. During this step, processing and control unit 105 implements a method of re-estimation of the time-dependent parameters of the model, taking into account the data relative to the insulin effectively injected by device 103 and the data relative to the real blood sugar measured by sensor 101 for a past observation period, for example a period from 1 to 10 hours preceding the calibration step. More particularly, during the calibration step, processing and control unit 105 simulates the patient's behavior over the past observation period based on the physiological model (taking into account possible glucose ingestions and insulin injections during this period) and compares the curve of the blood sugar estimated by the model with the curve of the real blood sugar measured by the sensor during this same period. Processing and control unit 105 then searches, for the time-dependent parameters of the model, a set of values leading to minimizing a quantity representative of the error between the curve of the blood sugar estimated by the model and the curve of the real blood sugar measured by the sensor during the observation period. As an example, the processing and control unit searches a set of parameters leading to minimizing an indicator m representative of the area between the curve of the blood sugar estimated by the model and the curve of the real blood sugar measured by the sensor during the observation period, for example defined as follows:

$$m = \frac{1}{\Delta T} \sum_{t=t_0}^{t_0+\Delta T} |g(t) - \hat{g}(t)|^2$$

where t is the discretized time variable, $t_0$ corresponds to the time of beginning of the past observation phase, $t_0+\Delta T$ corresponds to the end time of the past observation phase (for example corresponding to the time of beginning of the model calibration step), g is the curve of time variation of the real blood sugar measured by sensor 101 during period [$t_0$, $t_0+\Delta T$], and $\hat{g}$ is the curve of the blood sugar estimated based on the model during period [$t_0$, $t_0+\Delta T$]. The optimal parameter search algorithm used during this step is not detailed in the present application, the described embodiments being compatible with usual algorithms used in various field to solve problems of parameter optimization by minimization of a cost function.

The method of FIG. 4 further comprises, after step 401, a step 403 of prediction, by processing and control unit 105, of the evolution over time of the patient's blood sugar during a period to come, based on the physiological model updated at step 401, taking into account the history of insulin injected to the patient and the history of glucose ingested by the patient.

The method of FIG. 4 further comprises, after step 403, a step 405 of determining, by processing and control unit 105, taking into account the curve of the future blood sugar predicted at step 403, insulin doses to be injected to the patient for a period to come. At the end of this step, processing and control unit 105 may program injection device 103 to deliver the determined doses for the period to come.

Steps 403 of prediction of the blood sugar and 405 of determination of the future doses of insulin to be delivered may for example be repeated for each update of the physiological model (that is, after each iteration of step 401), for each new ingestion of glucose notified by the patient, and/or for each new administration of an insulin dose by injection device 103.

A problem which is posed in the above-described operation is that, on update of the physiological model at step 401, processing and control unit 105 should define a vector [INIT] of initial states (states at $t_0$) of the state variables of the model, to be able to simulate the patient's behavior from the model. Such initial states are necessary not only to be able to predict the future evolution of the patient's blood sugar (step 403), but also during the actual model update step (step 401) to be able to simulate the variation of the patient's blood sugar during the past observation period, to be able to compare the simulated blood sugar with the measured blood sugar.

To define the initial states of the state variables of the model, a first possibility comprises making the assumption that, in the period preceding the observation period [t0, $t_0+\Delta T$] having the model calibration based thereon, the patient was in a stationary state, with a constant injected insulin flow, and no dietary intake of glucose. Under this assumption, all the derivatives of the differential equation system can be considered as zero at initial time $t_0$. The values at $t_0$ of the state variables of the system can then be analytically calculated. A disadvantage of such a solution is that the output of the model (the estimated blood sugar) is not constrained. In particular, the blood sugar estimated at time $t_0$ may be different from the real blood sugar measured at time $t_0$. In this case, the algorithm implemented at step 401 for searching the time-dependent parameters of the model by minimizing the error between the simulated blood sugar and the measured blood sugar may have trouble converging.

To improve the initialization, a second possibility comprises making the same assumptions as previously, but constraining variable $Q_1(t_0)$ so that the blood sugar estimated at time $t_0$ is equal to the real blood sugar measured by the sensor. This enables to improve the relevance of the initialization at time $t_0$. However, at time $t_0$, the derivative of the estimated blood sugar and the derivative of the real blood sugar may diverge. Accordingly, the algorithm for searching for the time-dependent parameters of the system may here again have trouble converging.

In practice, the two above-mentioned methods of determining the initial states of the physiological model are often unsatisfactory, which makes it difficult to search for a set of values relevant for the time-dependent parameters of the model. A consequence is that the forecasts of the future evolution of the patient's blood sugar based on the model may be erroneous and result in a poor regulation of the blood sugar by the system.

To overcome this problem, according to an aspect of an embodiment, it is provided, during the model calibration or update phase (step 401), to consider the initial states [INIT] of the model as random variables, and to perform, as it is done to estimate the time-dependent parameters of the model, a search for an optimal set of values of initial states by minimization of a quantity representative of the error between the curve of the blood sugar estimated by the model and the curve of the real blood sugar measured by the sensor during the observation period having the calibration based thereon.

If the cumulated number of the time-dependent parameters and of the state variables of the physiological model is sufficiently low, the optimal values of the time dependent parameters and of the initial states of the state variables may be determined simultaneously, during a same step of optimization of the model by minimization of the error between the estimated blood sugar and the real blood sugar over the past observation period.

In practice, in Hovorka's model, as well as in most physiological models describing the assimilation of insulin and of glucose by the body and their impact on blood sugar, the cumulated number of the time-dependent parameters and of the state variables is relatively large, which may result in a numerical instability during the phase of search for optimal values. In other words, certain values may be difficult, or even impossible, to estimate in a single search, there being too many unknowns. In this case, the problem may be broken up into two sub-problems, respectively corresponding to the estimation of the time-dependent parameters of the model and to the estimation of the initial states of the model, as will now be described in relation with FIG. 5.

Figure 5:
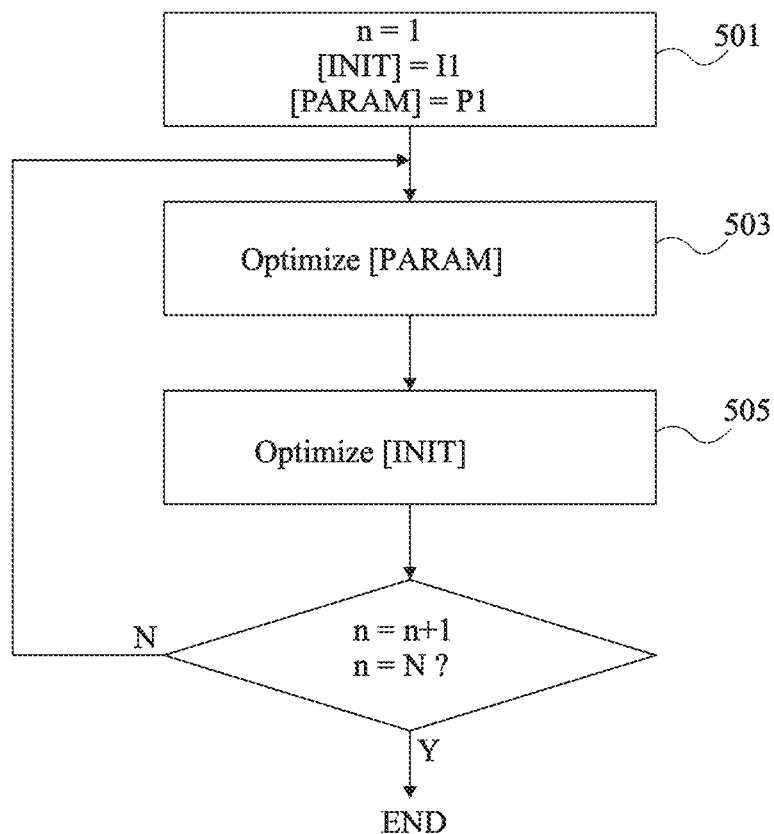
FIG. 5 is a diagram illustrating an embodiment of an automated calibration method implemented by the system of FIG. 1.

FIG. 5 is a diagram illustrating an embodiment of an automated method of calibration or of update of the system of FIG. 1, corresponding to an embodiment of step 401 of FIG. 4.

This method comprises a step 501 during which the parameter vector [PARAM] (here reduced to the time-dependent parameters of the model only) is initialized to a first set of values P1. Set P1 for example corresponds to the values taken by parameters [PARAM] before the beginning of the model update phase. As a variation, the set of values P1 is a predetermined reference set, for example corresponding to the average values taken by parameters [PARAM] over a reference period. During step 501, the vector of initial states [INIT] of the state variables is further initialized to a first set of values I1. The set of values I1 is for example analytically determined as described hereabove, by making the assumption of a stationary state of the patient in the period preceding the calibration phase, and by having the blood sugar estimated at time $t_0$ coincide with the real blood sugar measured at this same time.

During a step 503 subsequent to step 501, processing and control unit 105 searches, by setting the set of initial states [INIT] to its current state, a set of values of the time-dependent parameters of the model resulting in minimizing a quantity representative of the error between the curve of the blood sugar estimated based on the model and the curve of the real blood sugar during the observation period, for example, indicator m defined hereabove. At the end of this step, vector [PARAM] is updated with the new estimated values.

During a step 505 subsequent to step 503, processing and control unit 105 searches, by setting the set of parameters [PARAM] to its current state, a set of values of initial states of the state variables resulting in minimizing a quantity representative of the error between the blood sugar curve estimated based on the model and the curve of the real blood sugar during the observation period, for example, the indicator m defined hereabove, or any other indicator representative of the error between the two curves, for example, an indicator based on the L1 norm. At the end of this step, vector [INIT] is updated with the new estimated values.

In this example, steps 503 and 505 are repeated a predetermined number N of times, where N is an integer greater than 1. The values of the time-dependent parameters and of the initial states of the updated model then correspond to the values of vectors [PARAM] and [INIT] at the end of the N-th iteration of steps 503 and 505. As a variation, it is possible for the number of iterations of steps 503 and 505 not to be predetermined, and to be adjusted by taking into account the evolution of indicator m of the error between the blood sugar estimated based on the model and the real blood sugar over the observation period.

The optimal value search algorithms used at steps 503 and 505 are not detailed in the present application, the described embodiments being compatible with usual algorithms used in various fields to solve problems of parameter optimization by minimization of a cost function.

An advantage of the above-described operating method, where the initial values of the state variables of the physiological model are determined by minimization of a quantity representative of the error between the measured blood sugar data and the estimated blood sugar during a past observation period, is that it enables to improve the quality of the prediction of the patient's future blood sugar, and thus to more relevantly control insulin intakes.

An object of another embodiment is to enable to limit risks for the patient due to a possible failure of the physiological model used to predict the patient's future blood sugar.

For this purpose, according to an aspect of an embodiment, the control and processing device 105 of the regulation system is capable, after each update or recalibration of the physiological model (step 401), of estimating the quality of the updated physiological model by means of one or of a plurality of numerical quality indicators and, if the quality of the model is considered unsatisfactory, of stopping using the model to regulate the patient's blood sugar.

Figure 6:
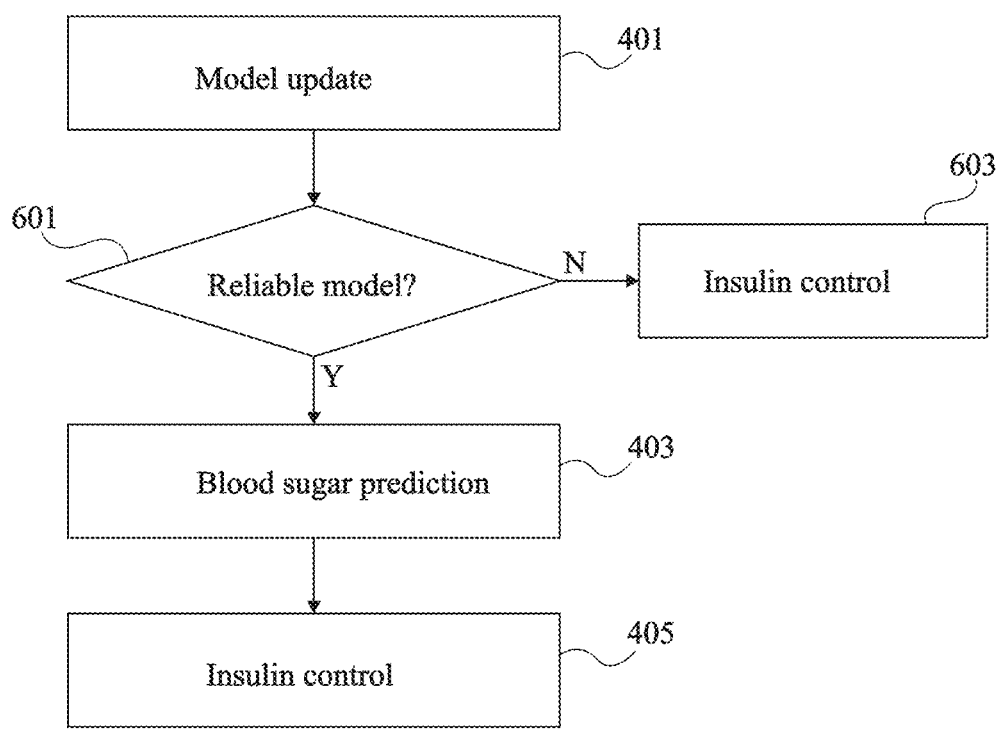
FIG. 6 is a diagram illustrating an embodiment of an automated blood sugar regulation system implemented by the system of FIG. 1.

FIG. 6 is a diagram illustrating an embodiment of an automated blood sugar regulation method implemented by the system of FIG. 1.

This method comprises the same steps 401, 403, and 405 as in the example of FIG. 4. However, the method of FIG. 6 further comprises, after each step 401 of update of the physiological model used by the regulation system and before the implementation of the following steps 403 of prediction of the patient's future blood sugar from the model and 405 of control of the insulin delivery based on the blood sugar prediction, a step 601 of verification of the quality of the updated model.

At step 601, processing and control unit 105 determines one or a plurality of numerical indicators of the quality of the model updated at step 401. As an example, the processing and control unit calculates a numeral quality indicator representative of the area between the curve of the blood sugar estimated based on the model and the curve of the real blood sugar measured by sensor 101 during a past observation period. This indicator for example corresponds to above-defined quantity m.

Instead of, or as a complement to, an indicator representative of the surface area between the estimated blood sugar and real blood sugar curves during a past observation period, processing and control unit 105 may calculate one and/or the other of the following quality indicators m1 and m2:

$$m_1(t_{current}) = g(t_{current}) - \hat{g}(t_{current})$$

$$m_2(t_{current}) = g'(t_{current}) - \hat{g}'(t_{current}),$$

where $t_{current}$ designates a present time of implementation of step 601 of verification of the quality of the model, g corresponds to the function of time variation of the real blood sugar measured by sensor 101, $\hat{g}$ corresponds to the function of time variation of the blood sugar simulated from the model, g' corresponds to the derivative of the function of time variation of the real blood sugar, and $\hat{g}'$ corresponds to the derivative of the function of time variation of the simulated blood sugar.

As an example, the quality of the model can be considered as satisfactory by processing and control unit 105 when values m, $m_1$ and $m_2$ are smaller than predetermined thresholds. More generally, any other quality criterion or any other combination of quality criteria may be used at step 601 to determine whether the physiological model recalibrated at step 401 can be considered as reliable.

If the physiological model is considered as reliable at step 601 (O), steps 403 and 405 can be implemented similarly to what has been previously described, that is, processing and control unit 105 continues following the predictions made by the physiological model to regulate the delivery of insulin to the patient.

If the physiological model is considered insufficiently reliable at step 601 (N), processing and control unit 105 stops using this model to regulate the delivery of insulin to the patient and implements a substitute regulation method at a step 603.

As an example, at step 603, processing and control unit 105 uses a simplified physiological model, for example, a compartmental model comprising a reduced number of state variables and a reduced number of parameters as compared with the initial model, to predict the evolution of the patient's blood sugar and accordingly regulate the insulin injection.

As a variation, at step 603, processing and control unit 105 stops implementing a predictive control, that is, it stops using a physiological model to predict the patient's future blood sugar and accordingly regulate the insulin injection. In this case, processing and control unit 105 for example controls insulin injection device 103 to deliver preprogrammed insulin doses, for example corresponding to a reference basal rate prescribed to the patient.

Such a substitution method may for example be used during a predetermined time period. At the end of this period, steps 401 of calibration of the main physiological model and 601 of estimation of the quality of the main physiological model may be repeated to, if the quality of the main physiological model is considered satisfactory, reactivate the use of this model to regulate the delivery of insulin to the patient.

It should be noted that the method of FIG. 6 is not limited to the embodiment described in relation with FIGS. 4 and 5, where the calibration of the physiological model comprises a step of determination of the initial values of the state variables of the model by minimization of a quantity representative of the error between the measured blood sugar data and the blood sugar estimated during an observation period, but may be used whatever the selected method of determination of the initial values of the state variables of the model.

Specific embodiments have been described. Various alterations, modifications, and improvements will occur to those skilled in the art. In particular, the described embodiments are not limited to the specific example of physiological model detailed in the present disclosure, that is, Hovorka's model, but are compatible with any physiological model describing the assimilation of insulin by a patient's body and its effect on the patient's blood sugar, for example, the model called Cobelli's model, described in the article entitled "A System Model of Oral Glucose Absorption: Validation on Gold Standard Data", of Chiara Dalla Man et al. (IEEE TRANSACTIONS ON BIOMEDICAL ENGINEERING, VOL. 53, No. 12, DECEMBER 2006).

The invention claimed is:

1. An automated system of regulation of a patient's blood sugar, comprising:
a blood sugar sensor;
an insulin injection device; and
a processing and control unit configured for predicting the future evolution of the patient's blood sugar from a physiological model and for controlling the insulin injection device by taking the prediction into account, wherein the processing and control unit is configured for:
a) implementing a step of automatic calibration of the physiological model by taking into account a history of the blood sugar measured by the sensor during a past observation period;
b) at the end of the calibration step, determining whether the model is satisfactory or not based on at least one numerical indicator representative of an error between the blood sugar estimated based on the model and the real blood sugar measured by the sensor; and
c) if the quality of the model is not satisfactory, controlling the insulin injection device without taking into account the prediction made from the model;
wherein said at least one numerical indicator comprises an indicator $m_2$ representative of the difference between the derivative of the blood sugar estimated from the model and the derivative of the blood sugar measured by the sensor at a given time.

2. The system of claim 1, wherein said at least one numerical indicator comprises an indicator m representative of the area between a first curve $\hat{g}$ representative of the time variation of the blood sugar estimated based on the model over the observation period, and a second curve g representative of the time variation of the blood sugar measured by the sensor over the observation period.

3. The system of claim 2, wherein indicator m is defined as follows:

$$m = \frac{1}{\Delta T} \sum_{t=t_0}^{t_0+\Delta T} |g(t) - \hat{g}(t)|^2$$

where t is a discretized time variable, $t_0$ is the time of beginning of the observation phase, and $t_0+\Delta T$ is the end time of the observation phase.

4. The system of claim 1, wherein said at least one numerical indicator comprises an indicator $m_1$ representative of the difference between the blood sugar estimated based on the model and the blood sugar measured by the sensor at a given time.

5. The system of claim 1, wherein, at step c), the control of the insulin injection device is a model predictive control based on a simplified physiological model.

6. The system of claim 1, wherein, at step c), the insulin injection device is controlled to deliver preprogrammed insulin doses corresponding to a reference basal rate prescribed to the patient.

7. The system of claim 1, wherein the physiological model comprises a differential equation system describing the time variation of a plurality of state variables, and wherein step a) of automatic calibration of the model comprises a step of estimation of parameters of the differential equation system by minimization of a quantity representative of the error, during a past observation period, between the blood sugar estimated based on the physiological model and the blood sugar measured by the sensor.

8. The system of claim 7, wherein step a) of automatic calibration of the model further comprises a step of determining initial values of the state variables.

9. A method of automated regulation of a patient's blood sugar, comprising:
a step of calculating, by means of a processing and control unit, a prediction of the future evolution of the patient's blood sugar based on a physiological model; and
a step of controlling of an insulin injection device by taking into account this prediction; the method further comprising:
a) a step of automatic calibration of the physiological model by taking into account a history of the blood sugar measured by a sensor during a past observation period;
b) at the end of the calibration step, a step of determination of the quality of the physiological model based on at least one numerical indicator representative of an error between the blood sugar estimated based on the model and the real blood sugar measured by the sensor; and
c) if the quality of the model is considered unsatisfactory, a step of control of the insulin injection device without taking into account the prediction made from the model;
wherein said at least one numerical indicator comprises an indicator $m_2$ representative of the difference between the derivative of the blood sugar estimated from the model and the derivative of the blood sugar measured by the sensor at a given time.

* * * * *

UNITED STATES PATENT AND TRADEMARK OFFICE
CERTIFICATE OF CORRECTION

PATENT NO. : 11,213,249 B2
APPLICATION NO. : 16/334812
DATED : January 4, 2022
INVENTOR(S) : Eléonore Maeva Doron Page 1 of 1

It is certified that error appears in the above-identified patent and that said Letters Patent is hereby corrected as shown below:

In the Claims

At Column 14, Claim 9, Line 33 please replace "of controlling of" with --of controlling--.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*